United States Patent [19]

Fischer

[11] Patent Number: 5,031,768
[45] Date of Patent: Jul. 16, 1991

[54] INSTRUMENT TRAY AND DISPOSABLE RECEPTACLE HAVING ALTERNATIVE LOCKING MEANS

[75] Inventor: Dan E. Fischer, Sandy, Utah
[73] Assignee: Ultradent Products, Inc., Salt Lake City, Utah
[21] Appl. No.: 506,677
[22] Filed: Apr. 9, 1990
[51] Int. Cl.⁵ .......................................... A61B 19/02
[52] U.S. Cl. .................................. 206/370; 206/364; 206/438; 206/571; 206/807; 220/306; 220/324; 220/339
[58] Field of Search ............................. 206/363–370, 206/438, 570–572, 564, 807; 220/306, 315, 324, 337, 339

[56] References Cited

U.S. PATENT DOCUMENTS

| | | | |
|---|---|---|---|
| D. 202,599 | 10/1965 | Goyke | D83/1 |
| D. 288,606 | 3/1987 | Blatherwick et al. | D24/31 |
| 2,659,485 | 11/1953 | Duley et al. | 206/564 X |
| 3,013,656 | 12/1961 | Murphy, Jr. | 206/571 X |
| 3,164,478 | 1/1965 | Bostrom | 220/337 X |
| 3,327,841 | 6/1967 | Schurman et al. | |
| 3,494,458 | 2/1970 | Meierhoefer | 206/366 |
| 3,645,758 | 2/1972 | MacManus | 220/306 X |
| 3,650,393 | 3/1972 | Reiss et al. | |
| 3,770,119 | 11/1973 | Hultberg et al. | |
| 4,013,109 | 3/1977 | Sandel | 206/370 |
| 4,170,300 | 10/1979 | Pick | 206/365 |
| 4,176,743 | 12/1979 | Fitzpatrick | 206/564 X |
| 4,193,496 | 3/1980 | Barratt | 220/306 X |
| 4,195,734 | 4/1980 | Boner et al. | 206/564 X |
| 4,266,669 | 5/1981 | Watson | 206/570 X |
| 4,444,332 | 4/1984 | Widen et al. | 220/306 |
| 4,523,679 | 6/1985 | Paikoff et al. | 206/370 |
| 4,541,992 | 9/1985 | Jerge et al. | 422/300 |
| 4,595,102 | 6/1986 | Cianci et al. | 206/572 |
| 4,746,008 | 5/1988 | Heverly et al. | 220/306 X |
| 4,784,267 | 11/1988 | Gessler et al. | 206/438 |
| 4,844,249 | 7/1989 | Coulombe | 206/438 |
| 4,874,103 | 10/1989 | Quisenberry et al. | 220/306 X |
| 4,886,165 | 12/1989 | Annett | 206/370 |
| 4,898,276 | 2/1990 | Georgakis | 206/370 X |
| 4,915,233 | 4/1990 | Smith | 206/571 |
| 4,928,830 | 5/1990 | Brewer | 206/570 X |

OTHER PUBLICATIONS

Advertisement entitled "Product Profiles" for Disposable Instrument Tray, *Dental Economics*, p. 91, May 1990, demonstrating a disposable, multi-feature set-up tray.
Advertisement for "Dapway", Crescent Dental Mfg., Co., St. Lyons, IL, *Dental Economics*, Apr. 1989, p. 38, showing disposable dappen and mixing dish inserts.
Advertisement for "The Healthpak Dental Tray", HealthPak, Inc., Joliet, IL, *Dental Products Report*, Oct. 1988, showing a disposable tray.
Advertisement for "needle-cap holder", Preventative Systems, Ltd.
Page No. 240 from Darby equipment catalog entitled "Trays for Instruments," showing autoclavable set-up trays.
Advertisement entitled "Miscellaneous — Trays & Racks," showing instrument set-up trays.
Advertisement entitled "Miscellaneous/Sundry—Instrument Trays."
Advertisement entitled "Instrument Trays," showing autoclavable plastic trays.
Advertisement for "The HealthPak Dental Tray", HealthPak, Inc., Joliet, IL, showing a disposable dental instrument tray.

*Primary Examiner*—Bryon P. Gehman
*Attorney, Agent, or Firm*—Workman Nydegger Jensen

[57] ABSTRACT

A hinged instrument tray and disposable receptacle for contaminated waste. The tray is formed in two halves which are joined by a hinge so that the two halves of the tray can be opened and laid side-by-side thereby permitting access to the instruments contained within the tray. Contaminated materials or instruments can be collected in one or both halves of the tray so that when use of the instruments or materials is completed, the two tray halves can then be folded one on top of the other and the two tray halves can then be permanently locked together so as to enclose the contaminated instruments or materials therewithin, thereby forming a secure, tamper-proof disposable receptacle.

42 Claims, 5 Drawing Sheets

INSTRUMENT TRAY AND DISPOSABLE RECEPTACLE HAVING ALTERNATIVE LOCKING MEANS

BACKGROUND

1. The Field of the Invention

This invention relates to apparatus for providing a substantially contamination-free environment for storing sterilized or clean instruments and for thereafter also providing a receptacle for safe and contamination-free disposal of contaminated medical supplies, disposable syringes, and other medical sharps. More particularly, the present invention is directed to a hinged instrument tray for conveniently organizing instruments and keeping them ready for use, and/or to a tray which can also double as a disposable receptacle in which contaminated materials be placed after their use and then safely locked so as to render them tamper-proof and hence prevent contamination from them.

2. Description of the State of the Art

A number of medical and dental procedures, especially procedures requiring local or regional anesthesia, necessitate an antiseptic preparation of the skin of the patient, particularly when invasive procedures employing syringes, scalpels, or catheters are also involved. While not all such procedures require sterility, most often they are nonetheless clean procedures. In other words, while absolute sterility is not required in all cases, prevention of contamination or cross-contamination from one patient to another, or from a patient to the attending medical or dental personnel is essential.

In order to maintain the sterile or clean condition of medical and dental instruments to the greatest degree possible, currently available instrument trays employ a disposable drape or wrap to cover the instruments, a stackable configuration of trays to shield underlying instruments, or hinging systems so that the tray in one form or another folds back on itself to guard against contaminating environments.

While removable drapes and wraps are helpful in maintaining the sterility or cleanliness of instruments prior to their use, they offer little or no assistance in providing for a controlled disposal of contaminated instruments and/or supplies. Similarly, while stackable tray configurations offer some assistance in maintaining the sterility of instruments and implements, they must be separately handled and positioned when unstacked. Furthermore, stackable trays do not enclose all contaminated surfaces, instruments, and supplies without the further assistance of an additional cover-type apparatus.

Because many medical and dental procedures require that the instruments and supplies used become contaminated, and in light of the disposable nature of many instruments and supplies and the need for safe, effective disposal of such materials, it would be advantageous to have a medical or dental instrument tray which not only serves to conveniently house and store sterile or clean instruments and supplies, and to maintain the sterility or cleanliness as required by providing a contamination shield or barrier, but which also serves as a safe receptacle for the disposal of high risk waste such as spent and contaminated syringe needles, implements and other sharps and supplies.

Hinged trays currently available have several shortfalls. Such trays retain their ability and tendency to pivot at the hinge when the trays are opened flat for access to the instruments and supplies therein. Consequently, notwithstanding the fact that the tray halves are connected to each other by way of the hinge, the hinge neither fixes the angular relationship of the trays to each other, nor offers rigidity of structure when the tray is open.

It is advantageous during a medical or dental procedure to be able to quickly and confidently handle, position, reposition, or remove an open tray. The currently available hinged trays do not provide adequate rigidity for such handling, once opened. Thus, it would be a further advance in the art to be able to handle, position, reposition, or remove an open, hinged tray as if it were a unitized, rigid tray unit.

Most of the currently available instrument trays, whether hinged or not, provide a number of instrument racks on which sterile or clean instruments are placed in readiness for use. These racks serve to organize the necessary instruments and supplies needed in a given medical or dental procedure. Often, the instruments are organized in the order in which they are employed during the contemplated procedure.

Currently available trays generally simply provide parallel, side-by-side, coplanar instrument racks. Such a configuration of instrument racks is not optimal for all instruments and supplies. To the contrary, many instruments and supplies are of such a size, shape and/or character that what is needed is a racking system which provides for more customized access based on the instruments and supplies to be utilized.

For example, many medical and dental procedures require the use of syringes and other invasive instruments or sharps. It is desirable to provide a means for securing such syringes, invasive instruments and other sharps within the instrument tray so as to prevent accidental injury, yet it is also important to provide for ready access during the medical or dental procedure.

BRIEF SUMMARY AND OBJECTS OF THE INVENTION

The present invention seeks to resolve a number of the problems which have been experienced in the art, as identified above. More specifically, the apparatus of this invention constitutes an advance in the art of instrument trays, as evidenced by the following objects and advantages realized by the invention over the prior art.

One object of the present invention is to provide a hinged instrument tray which, when closed for storage of instruments prior to their use, inhibits the contamination of sterile and clean instruments, and which can also be secured in a closed position for safe, tamper-proof controlled disposal of high risk waste.

Still another object of the present invention is to provide a hinged instrument tray which, when open, permits the hinged tray halves to be rigidly locked in relationship to each other so that the two halves function together as a unitary, essentially rigid tray.

Yet another object of the present invention is to provide an instrument tray with improved instrument racks for securely holding instruments and supplies when the tray is either opened or closed, and which still provides for ready and easy access of such instruments and supplies.

A further object of the present invention is to provide an instrument tray with an improved rack for securing the positioning of medical and dental sharps within the instrument tray.

Additional objects and advantages of the invention will be apparent from the description and claims which follow, or may be learned by the practice of the invention.

Briefly summarized, the foregoing objects are achieved by an apparatus which comprises a tray having a base and sidewalls forming a tray interior, the tray interior having raised interior walls or partitions to divide the base into a plurality of compartments.

The apparatus of the present invention also includes an instrument rack system. The rack system has a plurality of substantially side-by-side, coplanar nesting compartments. The nested compartments or racks are offset such that the tail of nested instruments in one rack lie between the heads of instruments in the adjacent racks, and such that the rack itself, a sidewall, or some other partition serves as a stop to prevent the longitudinal displacement of the nested instrument in each rack. The instrument tray also permits the holding of an instrument in a plane other than the plane of the rack system in which other instruments are held to increase accessibility thereof.

In order to secure the position of syringes, other invasive instruments and other sharps, the tray of the present invention may also comprise a means for securely holding such instruments in place by using a notch configuration located in a sidewall or raised partition of the tray.

The tray of the present invention also comprises two halves with a hinge to join the two halves. One half may be folded to cover the other to inhibit contamination of sterile or clean instruments and supplies placed in the tray by employing a novel locking means.

In one position a locking means permits the folded tray to be opened, while in a second position, the locking means provides for locking the two halves in a closed configuration such that the two halves, one acting as a bottom and one acting as a top, are irreversibly locked in the closed position resulting in a secure, tamper-proof, sealed waste receptacle for the disposal of contaminated or high risk waste.

The hinged tray also comprises a latching means to rigidly fix the angular relationship of the two halves when opened. The latching means fixes the two halves in an open, substantially flat position resulting in a unitary rigid tray capable of being safely and confidently handled, positioned, repositioned, or moved by handling either half independently of the other.

DETAILED DESCRIPTION OF THE PRESENTLY PREFERRED EMBODIMENT

Reference is next made to a detailed description of the drawings which illustrate one presently preferred embodiment and the presently understood best mode for making and using the present invention. The following detailed description should be understood, however, to be only illustrative and not limiting of the scope of the invention as set forth in the appended claims.

Figure 1:
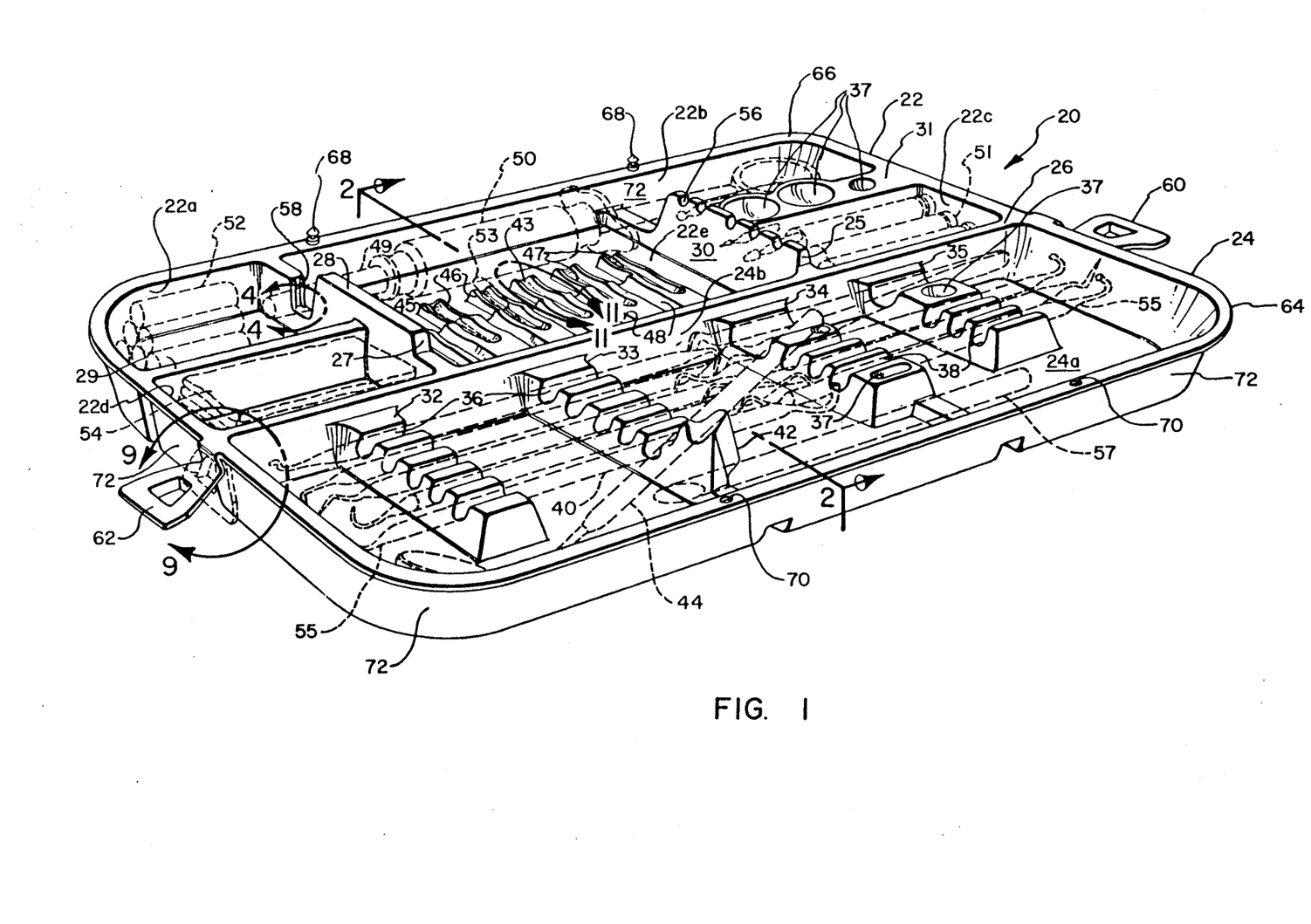
FIG. 1 is a perspective view of one presently preferred embodiment of the hinged instrument tray and disposable receptacle of the present invention, showing the tray in an open, essentially flat configuration.

With reference to FIG. 1, the hinged instrument tray and disposable receptacle is generally designated at 20. In the presently preferred embodiment, tray 20 is illustrated with a design that is particularly suited for organizing dental instruments of both a disposable and non-disposable variety, as well as various other types of dental materials and supplies. It should be understood, however, that the illustrated application of the inventive concept as defined in the appended claims is not necessarily limited to use of the hinged tray and disposable receptacle of the present invention to use as a dental tray. The tray and disposable receptacle of the present invention is equally suited for use in connection with medical instruments and supplies, as well as other potential industrial applications requiring the organization of sterile or clean instruments or supplies and materials as well as the potential disposal of contaminated materials.

In this sense, it is to be noted that the tray of the present invention serves a dual purpose. First, the tray serves as a means for permitting instruments to be conveniently organized and stored so as to maintain sterility or cleanliness of such instruments or materials and supplies by permitting the tray to be folded into a closed configuration so that the instruments contained therein are protected from the environment and hence from contamination prior to use. Second, the tray of the present invention is also designed so that it provides a means for collecting and disposing contaminated waste by permitting the tray to be folded into a locked, tamper-proof disposable receptacle which can not be reopened once the tray is closed and permanently locked. Accordingly, any application for the tray of the present invention, whether it be for use in connection with dental, medical or other industrial-type applications which require this type of dual purpose is intended to be within the scope of the present invention as described and claimed.

In accordance with the foregoing intended purposes and uses of the present invention, the hinged instrument tray and disposable receptacle of the present invention is comprised of a tray means for organizing and holding a plurality of items so that the items are easily accessible for individual removal and use. In the illustrated embodiment, the tray means comprise first and second trays 22 and 24 which are joined together by hinge 26. In the illustrated embodiment, the two trays 22 and 24 as well as hinge 26 are all formed of a unitary molded construction, although of course other ways of implementing the tray means could be devised, as for example molding separate trays and then joining them by a separate hinge mechanism.

With continued reference to FIG. 1, each tray 22 and 24 is comprised of a plurality of separate compartments formed on each tray and each compartment comprises means for holding and organizing at least one type of item. For example, tray 22 is illustrated as having formed therein by means of a unitary molded construction individual compartments 22a-22e. Separate compartments 22a-22e are formed by a plurality of interior walls 28-31 as well as by the side walls 72.

As shown by the various instruments and materials which are illustrated by the broken lines, each of the compartments 22a-22e can be utilized to organize and hold at least one type of instrument or other materials or supplies. For example, compartment 22a is illustrated as holding a plurality of cotton rolls 52, compartment 22b is designed to hold a syringe 50, compartment 22c is shown as holding a plurality of containers 51 containing various types of dental agents or compounds, compartment 22d is shown as containing gauze bandages or pads 54 and compartment 22e is shown as containing a racking system which holds a plurality of different kinds of endodontic files 53.

In similar fashion, tray 24 also comprises several compartments, as for example compartments 24a and 24b. Compartment 24b is defined by a plurality of walls 32-35 with slots 36 and 38 formed in the walls 32-35. The slots 36 and 38 are each designed to receive and hold various types of instruments 55 as hereinafter more fully described. Accordingly, walls 32-35 form a racking system for holding the instruments. Compartment 24 is designed to hold a separate type of instrument as shown at 57.

As will be appreciated from the illustration in FIG. 1, the walls 32-35 which form the racking system of compartment 24b are designed so that the slots or depressions 36 and 38 are offset from one another both longitudinally and laterally. Accordingly, the instruments 55 can thereby be situated in the depressions 36 and 38 in a manner such that the instruments that are held in depressions 36 will be laterally offset from the instruments which are held in the depressions 38 thereby rendering access to the various instruments more easy and efficient.

In the embodiment illustrated in FIG. 1 for example, instruments such as 55 are designed to be loaded into the racking system formed by the depressions 36 and 38 in walls 32-35 and then once the instruments are loaded, the entire tray may be partially closed, as hereinafter more fully described, and autoclaved. To assist in holding the instruments 55 once they have been placed into the racking system the walls 28 and 30 of tray 22 are each provided with a raised portion. For example, wall 28 has a portion of the wall 27 which is vertically raised and similarly wall 30 has a portion 25 which is vertically raised. As will be further appreciated from FIG. 1, each of the walls 28 and 30 are positioned so that when the tray 22 is folded over on top of tray 24 walls 28 and 30 will essentially bisect the space between walls 32 and 33 and the space between walls 34 and 35, respectively, which are situated in the bottom tray 24. Thus, as shown best in FIG. 3, the instruments which are held for example in the depressions 38 formed by walls 34 and 35 will also be at least partially secured so that they will be retained in the depressions 38 by means of the raised portion 25 of wall 30 when the upper tray 22 is folded over on top of the bottom tray 24. In a similar fashion, the raised portion 27 of wall 28 will also help to secure the instruments 55 that are held in the depressions 36 between walls 32 and 33 of tray 24.

As will be further seen from FIG. 1 some of the partition walls, as for example partition wall 31 of tray 22 and walls 34 and 35 of tray 24 are wide enough so that shallow receptacles 37 can be formed in the upper surface thereof for purposes of mixing and holding various kinds of compounds.

Figure 4:
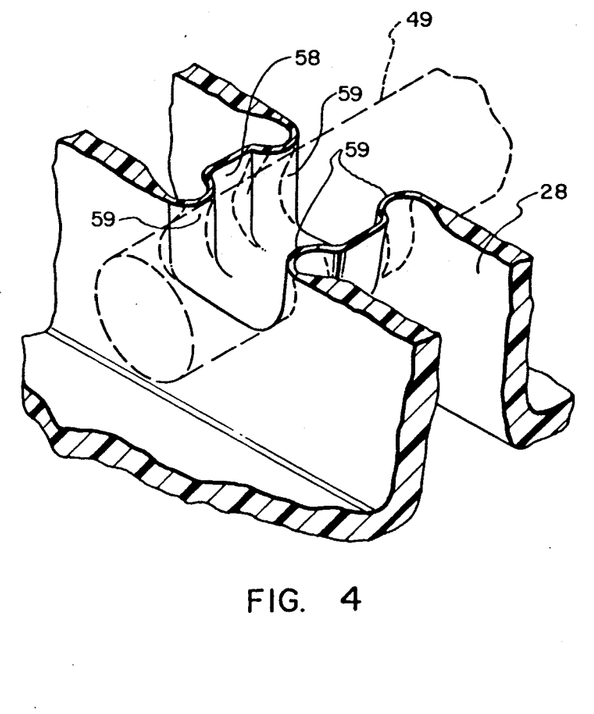
FIG. 4 is an enlarged portion cross-sectional view of a portion of one of the compartments of the tray, taken along line 4—4 of FIG. 1.
Figure 5:
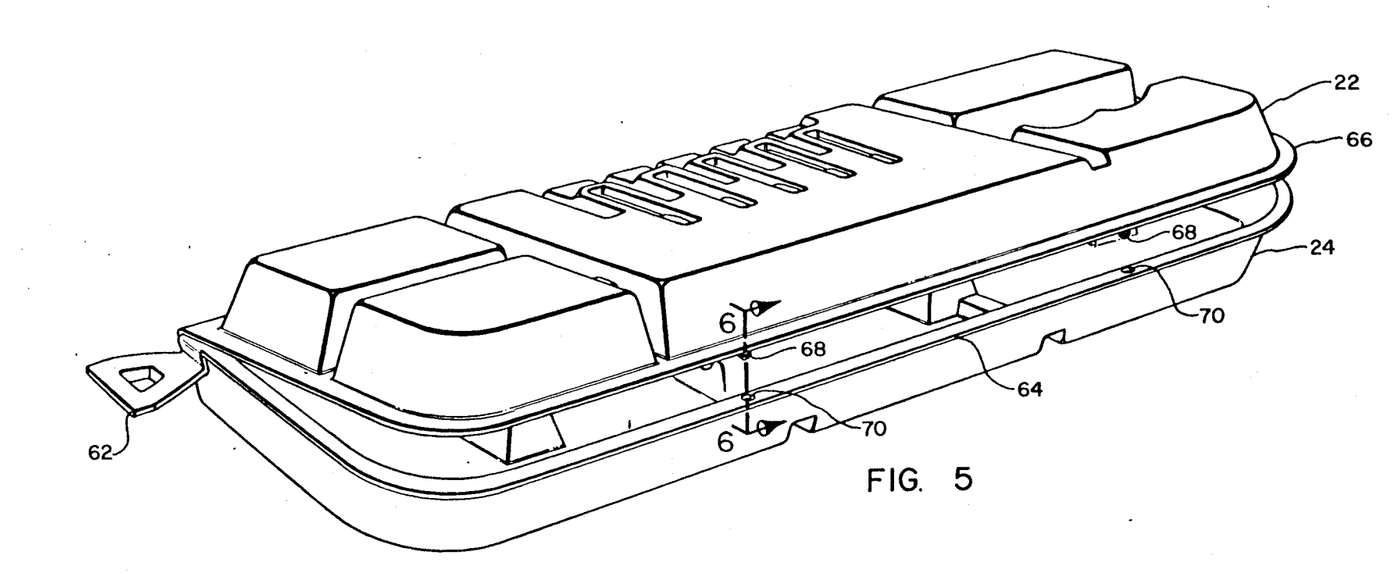
FIG. 5 is a perspective view illustrating the manner in which the tray halves may be folded so as to close the tray.

As further illustrated in FIG. 1, if desired some of the partition walls as for example partition walls 28 and 30 of tray 22 can be designed with notches or grooves such as illustrated at 58 and 56 for purposes of further securing or holding various types of instruments. As shown best in FIG. 4, partition wall 28 for example contains a notch 58 which has raised members 59 at the edges thereof which are designed to receive in a press-fit contact the protective cap of the syringe 50 so as to safely and securely hold the syringe 50 within the notch 58. Accordingly, the syringe 50 can be picked up and removed from the tray 22 without having to grasp the protective cap 49 so as to be able to remove the syringe from the protective cap. Furthermore, after the syringe has been used, the contaminated needle of the syringe 50 can be replaced into the protective cap 49 which will still be held securely in place in the tray by means of the press-fit notch 58. This advantageously minimizes the risk of someone using the syringe receiving an injury when trying to place the cap back onto the contaminated syringe needle and thus may help to prevent inadvertent contamination from such a puncture wound. Accordingly, as will be appreciated from the foregoing, the present invention may optionally comprise a means for frictionally receiving and securing at least one end of one of the items which is held in any one of the compartments of either of the trays, as in the case of the notch 58 in partition wall 28 of the presently preferred embodiment as shown in FIG. 1.

Figure 11:
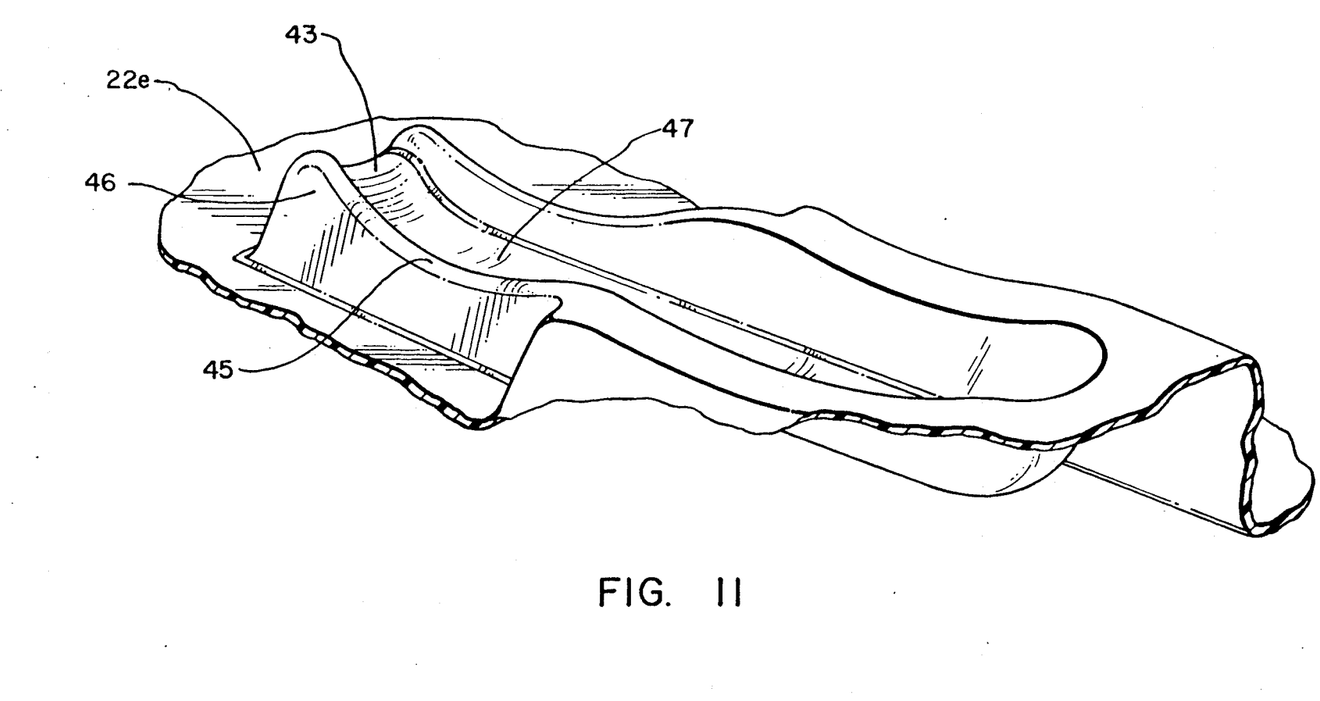
FIG. 11 is an enlarged perspective view of an individual well means which forms part of the racking system of one of the compartments in one of the trays of the present invention.

In a fashion similar to tray 24, the compartment 22e of tray 22 contains a racking system which permits of plurality of instruments, as for example endodontic files 53 to be held within compartment 22e. The racking system of compartment 22e is, however, designed somewhat differently in that there are a plurality of individual well means for cradling individual ones of the endodontic files. As shown in FIG. 1, each well means comprises longitudinal side members 46 which are sloped as at 45 to permit convenient access to the endodontic files 53. As will be further noted, each of the individual well means are laterally spaced to permit adequate space between them for accessing each separate instrument. As will be further noted from FIG. 1, one end of each of the individual well means is also sloped as shown, for example, at 43. The sloped end 43 is shown best in FIG. 11. As will be appreciated the sloped end 43 permits the endodontic file to be more easily removed simply by sliding the endodontic file up the gently sloped end 43 thereby vertically raising the end of the endodontic file sufficiently so that the instrument can be easily grasped along the portions of the sidewalls 46 which are curved or sloped as shown at 45. Accordingly, this greatly assists in the ease of accessing and removing such small instruments.

A further advantageous manner for arranging and holding the instruments when the tray is in the open, side-by-side configuration of FIG. 1 is illustrated in regard to the vertically raised platform 42 of tray 24. As shown, the vertically raised platform 42 permits an instrument such as the examination mirror 44 to be vertically raised at one end thereof so that such an instrument can be readily grasped. This particular type of raised platform 42 may thus be very helpful for providing access to an instrument such as the examination mirror 44 which is used more frequently than many of the other instruments held by the tray.

It is to be further noted from FIG. 1 that each of the interior walls or partitions 32–35 has a length that is somewhat shorter than the width of the tray 24 so that the compartment 24a can accommodate the storage of longer instruments such as, for example, a suction tube 57. Thus, as will be appreciated from the foregoing, the interior design of the various compartments of the instrument trays 22 and 24 can be designed to permit efficient access to the items or instruments held in the trays and which can also permit customization of the nature of the instruments and materials or supplies which are placed into and held by the trays.

The manner in which the hinged trays 22 and 24 can be opened and closed can be best understood by reference to FIGS. 2, 3 and 5–7 taken together. As shown in those figures, tray 22 is comprised of rim 66 which runs around the outer peripheral edge of the tray 22 and similarly tray 24 is comprised of a rim 64 which runs around its outer peripheral edge. A plurality of posts 68 are secured on rim 66 and a plurality of aligned apertures 70 are formed at corresponding locations on the rim 64. Thus, as shown best in FIGS. 5–7, when tray 22 is folded over on top of tray 24 each post 68 is inserted into a corresponding aperture 70.

Figure 2:
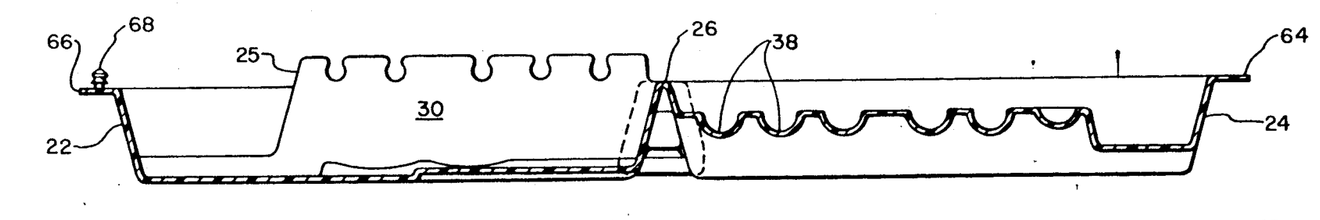
FIG. 2 is a cross sectional view taken along line 2—2 of FIG. 1.
Figure 3:
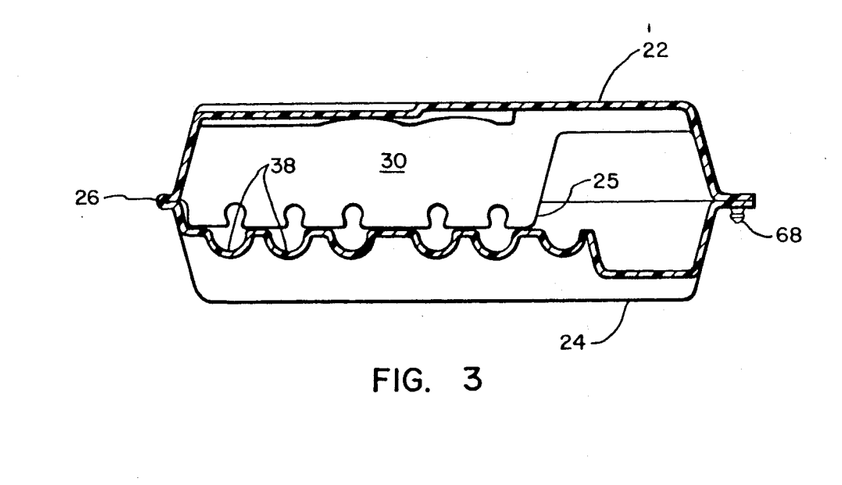
FIG. 3 is a cross sectional view taken along line 2—2 of FIG. 1, but illustrating the two tray halves folded one upon the other so as to form a closed tray.
Figure 6:
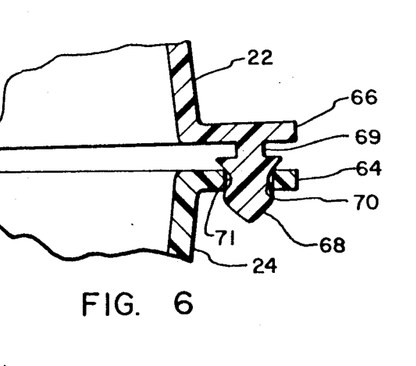
FIG. 6 is an enlarged cross-sectional view taken along line 6—6 of FIG. 5 showing the position of the tray halves when they are closed but not fully locked so that the tray halves can be reopened if desired.
Figure 7:
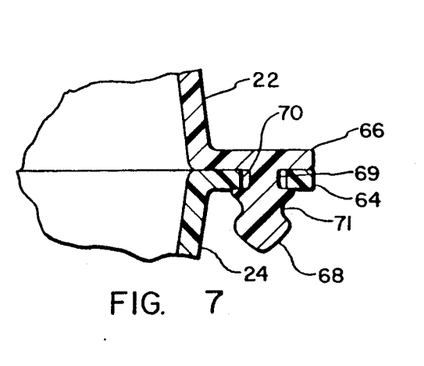
FIG. 7 is an enlarged cross-sectional view taken along line 6—6 of FIG. 5, but showing the tray halves in a fully locked position so as to form a closed, tamper-proof receptacle for contaminated waste.

As will be appreciated in reference to FIGS. 6 and 7, each post 68 contains two notched portions 71 and 69. The first notch 71 on post 68 is designed so that the post 68 can be both inserted into and removed from the aperture 70 when desired. Thus, when tray 22 is closed so that the post 68 is inserted to the point of the first notch 71 as shown in FIG. 6, the tray 22 can be reopened when it is desired to lay the trays in the flat, side-by-side configuration as shown in FIG. 2. However, when the tray 22 is folded over onto the tray 24 so that the post 68 is inserted to the point of notch 69, as shown in FIG. 7, the two trays 22 and 24 are then permanently locked so that the trays can not be reopened. In this position, the trays 22 and 24 are closed as shown in FIG. 3 so as to form a secure, tamper-proof disposable receptacle. Thus, contaminated materials or instruments which are of a disposable nature can be collected in the receptacle and then secured to prevent any further contamination from them.

Accordingly, as will be appreciated from the foregoing, the hinged instrument tray and disposable receptacle also comprises a locking means for selectively locking the trays in either of two positions when the trays are folded together to close them, one of the positions permitting the trays to be reopened and laid in a flat, side-by-side manner, and the other position preventing reopening of the trays so as to form a tamper-proof disposable receptacle for any contents enclosed therewithin when contamination-free disposal of the contents is desired. As will of course be appreciated, other arrangements for providing the desired locking means could be devised which could be equally effective as the illustrated post 68.

Figure 8:
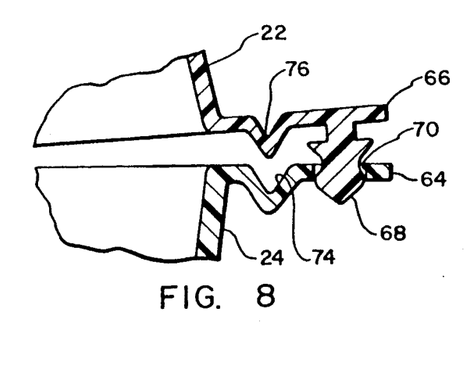
FIG. 8 is an enlarged cross-sectional view illustrating an alternative embodiment which includes an additional barrier for protection against leakage of contaminated liquids once the two tray halves are closed so as to form a locked, tamper-proof receptacle for disposal of contaminated waste.

If desired, further protection with respect to high risk waste which has been contaminated can be provided by including a barrier means formed at the peripheral edges of each tray for preventing escape of contaminated liquids when the trays are locked to form the tamper-proof disposable receptacle. An alternative embodiment which includes such a barrier means is illustrated in FIG. 8, for example.

As shown in that figure, peripheral edge 64 of tray 24 comprises a groove 74 whereas peripheral edge 66 of tray 22 comprises a corresponding ridge 76 so that when the two trays are locked together the ridge fits into the groove and thereby provides an effective barrier of leakage to any contaminated liquids.

The hinged instrument tray and disposable receptacle of the present invention can also comprise a means for securing the two trays 22 and 24 relative to one another when they are opened and placed in the flat, side-by-side configuration such as illustrated in FIG. 1. The means for securing the two trays relative to one another is designed to hold the two trays 22 and 24 together and to prevent them from opening more than essentially 180°, so that an essentially unitary, rigid tray is formed which can be easily handled by picking up either tray 22 or 24 without spilling the contents of the other.

Figure 9:
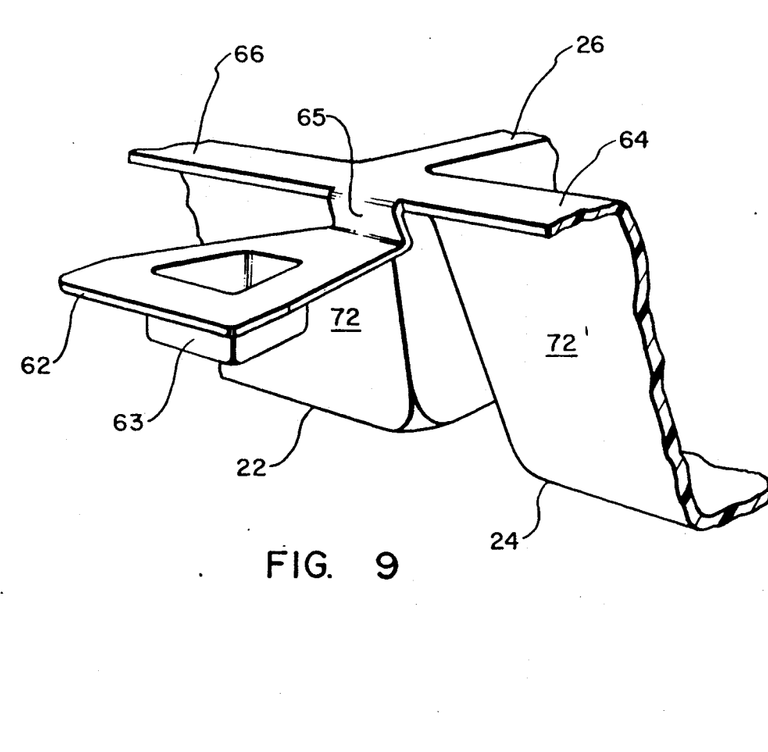
FIGS. 9 and 10 are enlarged perspective views with portions broken away, illustrating one end of the tray and in particular the latch means which is used to secure the two tray halves relative to one another when they are opened and placed in a side-by-side configuration so as to form an essentially unitary tray.
Figure 10:
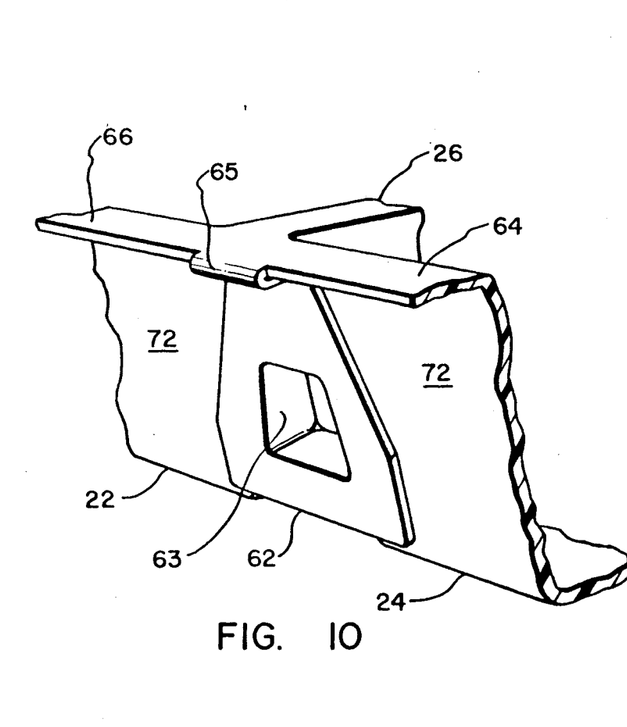

The means for securing the two trays is best illustrated in FIGS. 9 and 10. As shown in those figures, in the illustrated embodiment the means for securing the two trays relative to one another is comprised of a latch means situated at opposite ends of the hinge 26 and wherein each latch means comprises a hinged flap 62 formed by unitary molded construction with the two trays 22 and 24. Each hinged flap 62 also comprises an extension 63. The flap is joined by a hinge member 65 at the point where the two rims 66 and 64 come together at the point of hinge 26. Thus, as shown in FIG. 10 when the hinged flap 62 is folded down flat against the side walls 72, the extension 53 fits within the space formed between the side walls 72 of the two trays 22 and 24. Thus, extension 63 provides support and helps to secure the two trays 22 and 24 so that they will remain in an essentially flat, unitary relationship one to the other no matter which tray is picked up and handled independent of the other.

The present invention may be embodied in other specific forms without departing from the spirit or essential characteristics of the composition. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A hinged instrument tray and disposable receptacle for contaminated waste, comprising:

tray means for organizing and holding a plurality of items so that said items are easily accessible for individual removal and use, said tray means comprising first and second trays joined by a hinge such that said trays can be opened and laid in a substantially flat, side-by-side manner so as to render said items accessible, and such that said trays can be folded together so as to close any contents of said trays therewithin; and locking means for selectively locking said trays in either of two positions when said trays are folded together to close them, one of said positions permitting said trays to be re-opened and laid in said substantially flat, side-by-side manner, and the other said position preventing re-opening of said trays so as to form a tamper-proof disposable receptacle for any contents enclosed therewithin when contamination-free disposal of said contents is desired.

2. A hinged instrument tray and disposable receptacle for contaminated waste as defined in claim 1 wherein said tray means comprises a plurality of separate compartments formed on each said tray, each said compartment comprising means for holding and organizing at least one type of item.

3. A hinged instrument tray and disposable receptacle for contaminated waste as defined in claim 2 wherein at least one said compartment comprises rack means for holding a plurality of items of the same general type in side-by-side relation to one another, said rack means securing said items both laterally and longitudinally in relation to one another.

4. A hinged instrument tray and disposable receptacle for contaminated waste as defined in claim 3 wherein said rack means comprises a plurality of depressions formed within said compartment.

5. A hinged instrument tray and disposable receptacle for contaminated waste as defined in claim 4 wherein at least one of said depressions is formed so as to receive at least a portion of one of said items in a press-fit manner so as to frictionally hold said item therewithin.

6. A hinged instrument tray and disposable receptacle for contaminated waste as defined in claim 4 wherein at least some of said depressions are both laterally and longitudinally offset in relation to one another.

7. A hinged instrument tray and disposable receptacle for contaminated waste as defined in claim 1 wherein said trays each comprise a rim formed at a peripheral edge thereof, and wherein said locking means comprises a plurality of locking posts situated on a rim of at least one tray, and a plurality of corresponding apertures situated on a rim of the other tray, and wherein each said post comprises first and second notched portions such that when a post is inserted into a corresponding aperture to a point corresponding to said first notched portion, the inserted post can be removed from the corresponding aperture, and such that when a post is inserted into a corresponding aperture to a point corresponding to said second notched portion, the inserted post is locked into said corresponding aperture so it can not be removed.

8. A hinged instrument tray and disposable receptacle for contaminated waste as defined in claim 1 further comprising barrier means, formed at all peripheral edges of each said tray, for preventing escape of contaminated liquids when said trays are locked to form said tamper-proof disposable receptacle.

9. A hinged instrument tray and disposable receptacle for contaminated waste as defined in claim 8 wherein said barrier means comprises a groove formed in the peripheral edges of one said tray, and a corresponding ridge formed in the peripheral edges of the other tray, said ridge fitting into said groove when said trays are folded together to close them.

10. A hinged instrument tray and disposable receptacle for contaminated waste as defined in claim 1 further comprising means for securing said trays relative to one another such that when said trays are opened and laid in a substantially flat, side-by-side manner, said trays are held together and are prevented from opening more than about 180°.

11. A hinged instrument tray and disposable receptacle for contaminated waste as defined in claim 10 wherein said means for securing said trays comprises a latch means, situated at opposite ends of said hinge, for engaging and holding each said tray relative to the other.

12. A hinged instrument tray and disposable receptacle for contaminated waste as defined in claim 11 wherein each said latch means comprises a hinged flap, each said flap comprising an extension for insertion between said trays.

13. A hinged instrument tray and disposable receptacle for contaminated waste, comprising:

tray means for organizing and holding a plurality of items so that said items are easily accessible for individual removal and use, said tray means comprising first and second trays joined by a hinge such that said trays can be opened and laid in a substantially flat, side-by-side manner so as to render said items accessible, and such that said trays can be folded together so as to close any contents of said trays therewithin;

locking means for selectively locking said trays in either of two positions when said trays are folded together to close them, one of said positions permitting said trays to be re-opened and laid in said substantially flat, side-by-side manner, and the other said position preventing re-opening of said trays so as to form a tamper-proof disposable receptacle for any contents enclosed therewithin when contamination-free disposal of said contents is desired; and means for securing said trays relative to one another such that when said trays are opened and laid in a substantially flat, side-by-side manner, said trays are supported so as to form a unitary tray that can be picked up by handling either of said first and second trays, and which are prevented from opening more than about 180° by said securing means.

14. A hinged instrument tray and disposable receptacle for contaminated waste as defined in claim 13 wherein said trays each comprise a rim formed at a peripheral edge thereof, and wherein said locking means comprises a plurality of locking posts situated on a rim of at least one tray, and a plurality of corresponding apertures situated on a rim of the other tray, and wherein each said post comprises first and second notched portions such that when a post is inserted into a corresponding aperture to a point corresponding to said first notched portion, the inserted post can be removed from the corresponding aperture, and such that when a post is inserted into a corresponding aperture to a point corresponding to said second notched portion, the inserted post is locked into said corresponding aperture so it can not be removed.

15. A hinged instrument tray and disposable receptacle for contaminated waste as defined in claim 14 further comprising barrier means, formed at all peripheral edges of each said tray, for preventing escape of contaminated liquids when said trays are locked to form said tamper-proof disposable receptacle.

16. A hinged instrument tray and disposable receptacle for contaminated waste as defined in claim 15 wherein said barrier means comprises a groove formed in the peripheral edges of one said tray, and a corresponding ridge formed in the peripheral edges of the other tray, said ridge fitting into said groove when said trays are folded together to close them.

17. A hinged instrument tray and disposable receptacle for contaminated waste as defined in claim 13 wherein said means for securing said trays comprises a latch means, situated at opposite ends of said hinge, for engaging and holding each said tray relative to the other.

18. A hinged instrument tray and disposable receptacle for contaminated waste as defined in claim 17 wherein each said latch means comprises a hinged flap, each said flap comprising an extension for insertion between said trays.

19. A hinged instrument tray and disposable receptacle for contaminated waste as defined in claim 13 wherein said tray means comprises a plurality of separate compartments formed on each said tray, each said compartment comprising means for holding and organizing at least one type of item.

20. A hinged instrument tray and disposable receptacle for contaminated waste as defined in claim 19 wherein at least one said compartment comprises rack means for holding a plurality of items of the same general type in side-by-side relation to one another, said rack means securing said items both laterally and longitudinally in relation to one another.

21. A hinged instrument tray and disposable receptacle for contaminated waste as defined in claim 20 wherein said rack means comprises a plurality of depressions formed within said compartment.

22. A hinged instrument tray and disposable receptacle for contaminated waste as defined in claim 21 wherein at least one of said depressions is formed so as to receive at least a portion of one of said items in a press-fit manner so as to frictionally hold said item therewithin.

23. A hinged instrument tray and disposable receptacle for contaminated waste as defined in claim 21 wherein at least some of said depressions are both laterally and longitudinally offset in relation to one another.

24. A hinged instrument tray and disposable receptacle for contaminated waste, comprising:
first and second trays joined by a hinge such that said trays can be opened and laid in a substantially flat, side-by-side manner so as to render items therein accessible, and such that said trays can be folded together so as to close any contents of said trays therewithin, and wherein said trays each comprise a rim formed at a peripheral edge thereof; and
a plurality of locking posts situated on a rim of at least one tray, and a plurality of corresponding apertures situated on a rim of the other tray, and wherein each said post comprises first and second notched portions such that when a post is inserted into a corresponding aperture to a point corresponding to said first notched portion, the inserted post can be removed from the corresponding aperture, and such that when a post is inserted into a corresponding aperture to a point corresponding to said second notched portion, the inserted post is locked into said corresponding aperture so it can not be removed.

25. A hinged instrument tray and disposable receptacle for contaminated waste as defined in claim 24 further comprising barrier means, formed at all peripheral edges of each said tray, for preventing escape of contaminated liquids when said trays are locked to form a tamper-proof disposable receptacle.

26. A hinged instrument tray and disposable receptacle for contaminated waste as defined in claim 25 wherein said barrier means comprises a groove formed in the peripheral edges of one said tray, and a corresponding ridge formed in the peripheral edges of the other tray, said ridge fitting into said groove when said trays are folded together to close them.

27. A hinged instrument tray and disposable receptacle for contaminated waste as defined in claim 24 further comprising means for securing said trays relative to one another such that when said trays are opened and laid in a substantially flat, side-by-side manner, said trays are supported so as to form a unitary tray that can be picked up by handling either of said first and second trays, and which are prevented from opening more than about 180°.

28. A hinged instrument tray and disposable receptacle for contaminated waste as defined in claim 27 wherein said means for securing said trays comprises a latch means, situated at opposite ends of said hinge, for engaging and holding each said tray relative to the other.

29. A hinged instrument tray and disposable receptacle for contaminated waste as defined in claim 28 wherein each said latch means comprises a hinged flap, each said flap comprising an extension for insertion between said trays.

30. A hinged instrument tray and disposable receptacle for contaminated waste as defined in claim 24 further comprising a plurality of separate compartments formed on each said tray, each said compartment comprising means for holding and organizing at least one type of item.

31. A hinged instrument tray and disposable receptacle for contaminated waste as defined in claim 30 wherein at least one said compartment comprises rack means for holding a plurality of items of the same general type in side-by-side relation to one another, said rack means securing said items both laterally and longitudinally in relation to one another.

32. A hinged instrument tray and disposable receptacle for contaminated waste as defined in claim 31 wherein said rack means comprises a plurality of depressions formed within said compartment.

33. A hinged instrument tray and disposable receptacle for contaminated waste as defined in claim 32 wherein at least one of said depressions is formed so as to receive at least a portion of one of said items in a press-fit manner so as to frictionally hold said item therewithin.

34. A hinged instrument tray and disposable receptacle for contaminated waste as defined in claim 32 wherein at least some of said depressions are both laterally and longitudinally offset in relation to one another.

35. A hinged instrument tray and disposable receptacle for contaminated waste, comprising:

first and second trays joined by a hinge such that said trays can be opened and laid in a substantially flat, side-by-side manner so as to render items therein accessible, and such that said trays can be folded together so as to close any contents of said trays therewithin, and wherein said trays each comprise a rim formed at a peripheral edge thereof;

a plurality of locking posts situated on a rim of at least one tray, and a plurality of corresponding apertures situated on a rim of the other tray, and wherein each said post comprises first and second notched portions such that when a post is inserted into a corresponding aperture to a point corresponding to said first notched portion, the inserted post can be removed from the corresponding aperture, and such that when a post is inserted into a corresponding aperture to a point corresponding to said second notched portion, the inserted post is locked into said corresponding aperture so it can not be removed;

a latch means, situated at opposite ends of said hinge, for engaging and holding each said tray relative to the other, and wherein each said latch means comprises a hinged flap, each said flap comprising an extension for insertion between said trays.

36. A hinged instrument tray and disposable receptacle for contaminated waste as defined in claim 35 further comprising barrier means, formed at all peripheral edges of each said tray, for preventing escape of contaminated liquids when said trays are locked to form said tamper-proof disposable receptacle.

37. A hinged instrument tray and disposable receptacle for contaminated waste as defined in claim 36 wherein said barrier means comprises a groove formed in the peripheral edges of one said tray, and a corresponding ridge formed in the peripheral edges of the other tray, said ridge fitting into said groove when said trays are folded together to close them.

38. A hinged instrument tray and disposable receptacle for contaminated waste as defined in claim 37 further comprising a plurality of separate compartments formed on each said tray, each said compartment comprising means for holding and organizing at least one type of item.

39. A hinged instrument tray and disposable receptacle for contaminated waste as defined in claim 38 wherein at least one said compartment comprises rack means for holding a plurality of items of the same general type in side-by-side relation to one another, said rack means securing said items both laterally and longitudinally in relation to one another.

40. A hinged instrument tray and disposable receptacle for contaminated waste as defined in claim 39 wherein said rack means comprises a plurality of depressions formed within said compartment.

41. A hinged instrument tray and disposable receptacle for contaminated waste as defined in claim 40 wherein at least one of said depressions is formed so as to receive at least a portion of one of said items in a press-fit manner so as to frictionally hold said item therewithin.

42. A hinged instrument tray and disposable receptacle for contaminated waste as defined in claim 40 wherein at least some of said depressions are both laterally and longitudinally offset in relation to one another.

* * * * *